United States Patent [19]
Zavareh

[11] Patent Number: 6,121,453
[45] Date of Patent: Sep. 19, 2000

[54] RESOLUTION OF THREO-METHYLPHENIDATE

[75] Inventor: Hooshang Shahriari Zavareh, Cambridge, United Kingdom

[73] Assignee: Medeva Europe Limited, United Kingdom

[21] Appl. No.: 09/142,486

[22] PCT Filed: Mar. 7, 1997

[86] PCT No.: PCT/GB97/00643

§ 371 Date: Sep. 8, 1998

§ 102(e) Date: Sep. 8, 1998

[87] PCT Pub. No.: WO97/32851

PCT Pub. Date: Sep. 12, 1997

[30] Foreign Application Priority Data

Mar. 8, 1996 [GB] United Kingdom .................. 9604943

[51] Int. Cl.[7] ................................................. C07D 211/34
[52] U.S. Cl. ................................................ 546/238
[58] Field of Search ................................................ 546/238

[56] References Cited

U.S. PATENT DOCUMENTS 2,957,880  10/1960  Rometsch et al. ...................... 260/294
4,196,303  4/1980  Kane et al. .............................. 560/126

FOREIGN PATENT DOCUMENTS 55038363  3/1980  European Pat. Off. ............... 546/238

OTHER PUBLICATIONS

Chemical Abstract vol. 111 No. 115678, Ozaki et al., "Synthesis of Inositol Polyphosphates" (1989).
Chemical Abstract vol. 124 No. 175974, Miyauchi et al, Optical resolution of dl–threa2 (2,4 difluoropharol)–2C1 methyl.

*Primary Examiner*—John Kight
*Assistant Examiner*—R. Covington
*Attorney, Agent, or Firm*—Saliwanchik, Lloyd & Saliwanchik

[57] ABSTRACT

A process for preparing substantially single enantiomer d-threo-methylphenidate, proceeds by means of a classical salt resolution using (−)-menthoxyacetic acid.

1 Claim, No Drawings

RESOLUTION OF THREO-METHYLPHENIDATE

FIELD OF THE INVENTION

This invention relates to the resolution of threo methylphenidate via crystallisation of diastereomeric salts.

BACKGROUND OF THE INVENTION

Methylphenidate was first prepared as a mixture of the erythro and threo racemates. U.S. Pat. No. 2,957,880 discloses studies upon the two racemic mixtures, which revealed that the therapeutic activity resides in the threo diastereomer.

The resolution of threo methylphenidate can be achieved using the expensive resolving agent 1,1'-binaphthyl-2,2'-diylhydrogen phosphate, a process first reported by Patrick et al (The Journal of Pharmacology and Experimental Therapeutics, 241:152–158 (1987)), and subsequently used by other workers in the field (e.g. Aoyama et al, Journal of Chromatography, 494:420 (1989)). This is perceived to be a more efficient procedure than the method disclosed in U.S. Pat. No. 2,957,880, wherein the corresponding amide of erythro methylphenidate (i.e. R—$CONR_2$ rather than R—$CON_2Me$) is resolved with tartaric acid prior to amide hydrolysis and equilibration at the benzylic centre, followed by esterification of the resultant threo-acid.

An improved resolution process is described in PCT/GB97/00185. Such a resolution can be combined with the racemisation described in PCT/GB97/00281.

SUMMARY OF THE INVENTION

This invention is based upon the discovery that racemic threo methylphenidate can be resolved using inexpensive (−)-menthoxyacetic acid.

DESCRIPTION OF THE INVENTION

The process of this invention may be carried out under conditions that are generally known to those skilled in the art of classical salt resolution procedures. For example, a mixture of threo methylphenidate free base and 1 molar equivalent of (−)-menthoxyacetic acid in an inert organic solvent is heated and then allowed to cool; the resultant precipitate is filtered, washed with an appropriate solvent and dried to afford directly a salt enriched in 98% ee d-threo methylphenidate. This is a great improvement on the literature method using 1,1'-binaphthyl-2,2'-diylhydrogen phosphate, described by Patrick et al, supra, in which the first crystallisation gave a salt corresponding to 85–90% ee material, and further recrystallisation of this material was necessary to raise the ee to 95–97%. The latter level of optical purity is achieved in the present invention in one crystallisation, with an overall higher yield. The method of this invention is therefore more efficient and more economical than the one described by Patrick et al.

The following Example illustrates the resolution of threo methylphenidate using (−)-menthoxyacetic acid.

EXAMPLE dl-threo methylphenidate (1.0 g, 3.7 mmol) was suspended in water (20 ml) and treated with caustic solution. The liberated free base was extracted with MTBE (3×25 ml), dried over $MgSO_4$ and evaporated to a light oil. This was dissolved in IPA (15 ml) and heated to 60° C. (−)-Menthoxyacetic acid (0.79 g, 3.79 mmol) in IPA (5 ml) was added. Heating was continued for a further 30 min and the mixture was gradually cooled to 10° C. The resulting white crystalline product was filtered off, washed with cold IPA and dried (0.85 g, 47% by weight, corresponding to 98% ee d-threo methylphenidate, as determined by chiral HPLC after salt cracking).

What is claimed is:

1. A process for preparing substantially single enantiomer d-threo-methylphenidate, which proceeds by means of a classical salt resolution using (−)-menthoxyacetic acid.

* * * * *